United States Patent [19]

Strickland

[11] Patent Number: 4,937,889
[45] Date of Patent: Jul. 3, 1990

[54] FEMALE URINAL

[76] Inventor: Maxine R. Strickland, 6606 Rowan, Houston, Tex. 77074

[21] Appl. No.: 353,229

[22] Filed: May 12, 1989

Related U.S. Application Data

[63] Continuation of Ser. No. 98,452, Sep. 18, 1987, abandoned.

[51] Int. Cl.$^5$ .............................................. A47K 11/00
[52] U.S. Cl. ........................................ 4/144.3; 4/144.2
[58] Field of Search .............................. 4/144.1–144.4; D24/54, 57; 128/761; 604/329, 356

[56] References Cited

U.S. PATENT DOCUMENTS

| D. 45,946 | 6/1914 | Meyer | D24/57 |
| D. 293,377 | 12/1987 | Chadbourne | D24/54 |
| 698,419 | 4/1902 | Taylor | 4/144.3 |
| 977,903 | 12/1910 | Ross | 4/144.3 |
| 3,329,973 | 7/1967 | Bobbe | 4/144.4 X |
| 4,309,779 | 1/1982 | Knight | 4/144.3 |
| 4,696,067 | 9/1987 | Woodward | 4/144.4 X |

FOREIGN PATENT DOCUMENTS 2164553  3/1986  United Kingdom ................. 4/144.3

Primary Examiner—Charles E. Phillips
Attorney, Agent, or Firm—Kirk, Bissex & Lindsay

[57] ABSTRACT

In one example embodiment, a female urinal is disclosed that includes a generally rectangular open container having a flat bottom portion with generally upright continuous side and end walls. One transverse end includes an upwardly and outwardly slanting wall cooperating with the adjacent side walls to provide a drainage ramp into the interior of the container. The other transverse end carries an indented shoulder disposed in the bottom and adjacent the end wall for permitting easy hand grasping of the urinal for transporting after use.

9 Claims, 2 Drawing Sheets

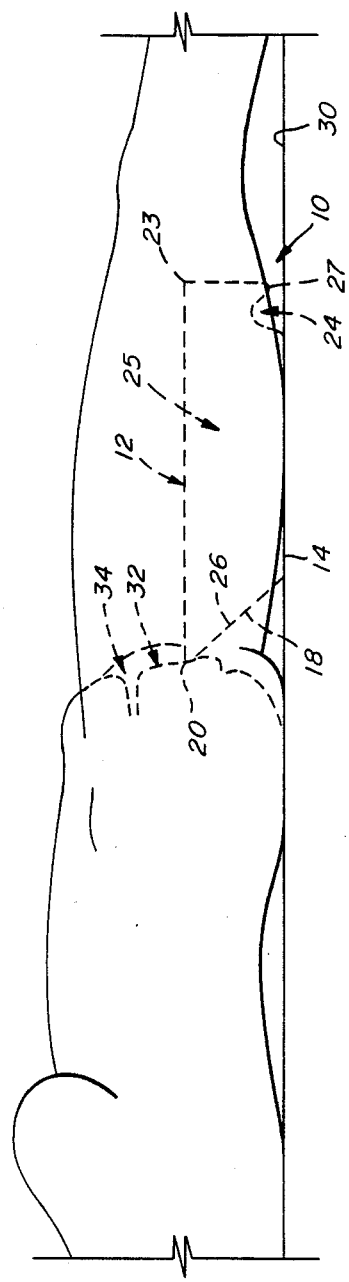
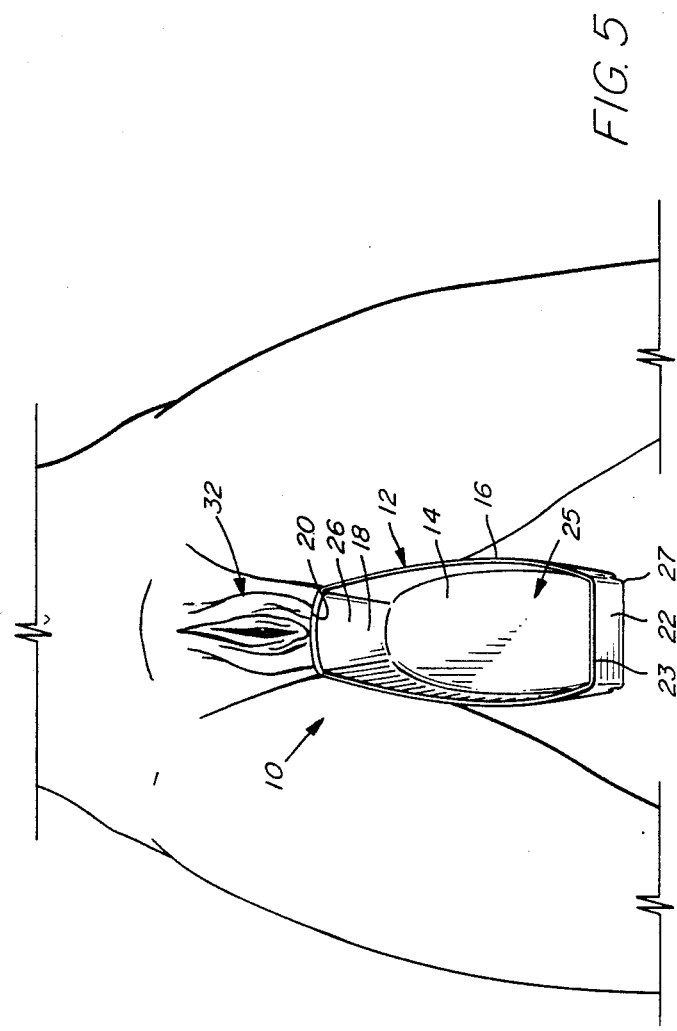
FIG. 4
FIG. 5

FEMALE URINAL

BACKGROUND OF THE INVENTION

This is a continuation, of application Ser. No. 07/098,452 filed Sept. 18, 1987.

This invention relates to urinal devices and, specifically, to a personal urinal for females.

Various urinal devices have long been used for collecting urine from both males and females over the years, from the universally used bed pan to a personal urinal developed to be used by both males and females, such as that disclosed in U.S. Pat. No. 4,309,779. There are a number of urinal designs that have been used by males and which remain relatively standardized due to the ease with which urine discharged from the penis can be collected. Use of cylindrical sleeves or funnel-like devices attached to a container into which the penis can be inserted completely collects all discharged urine flowing through the sleeve or funnel-like element.

However, attempts to develop a urinal that may be used by both males and females has met with limited success. To effectively and completely capture urine from a female requires a radically different structure than that required for males. It is more difficult to completely capture urine from a female urethra, particularly when the female is in a reclining position that is normal for patients that are ill or bed-ridden in hospitals, nursing homes, convalescent homes or at home. Prior female urinals or combination male/female urinals when used by reclining females suffered from the problem of how to avoid leakage and spillage that would soil the patient and the bed and bed coverings. Further, the combination male/female urinals are often cumbersome and complex and hard to be manipulated by the patient or only one other person.

Other attempts to provide a female urinal include a closed vessel having a bed pan shape and an extending neck with a mouth to completely surround the vulva of the user (U.S. Pat. No. 2,542,276) and a female urinal having an opening defined by a horizontal shelf to catch dripping urine and a vertical shroud to catch a horizontal stream of urine (U.S. Pat. No. 2,582,398). All of these various urinal devices can work, but are cumbersome, hard to use and their enclosed container shapes and flared necks and mouths make their manufacture expensive.

Still the most commonly used urinal device is the age-old bed pan or an updated variation of it. If the female user is heavy and/or because of the nature of an illness or injury is unable to move her legs and hips, it can take two or more persons to move the user sufficiently to be able to insert a bed pan under the user and to remove the bed pan later. Further, on occasion, nurses may inadvertently leave a female patient on a bed pan for some time which is extremely uncomfortable for the patient.

Accordingly, one primary feature of the present invention is to provide a urinal device that is shaped and dimensioned for use by a reclining female.

Another feature of the present invention is to provide a female urinal device that does not require lifting of the patient's body to use.

Yet another feature of the present invention is to provide a female urinal that is simple to use and can be positioned by the female user herself or any other assistant without special training.

Still another feature of the present invention is to provide a female urinal that is strong, lightweight and inexpensive to manufacture.

BRIEF SUMMARY OF THE INVENTION

The present invention remedies the problems of the prior art by providing a urinal for use by a female when reclining in a prone position in a bed or the like, comprising a generally rectangular or boat-shaped open container having a longitudinal axis substantially longer than the transverse axis, the width of the container having a dimension selected for comfortable placement between the upper thighs of the user when in the reclining position on a bed or the like, the open container comprising a relatively flat bottom portion and continuous side and end walls integrally attached to the bottom portion and extending upwardly therefrom.

In accordance with another principle of this invention, one of the transversely disposed end walls slants upwardly and outwardly from the bottom portion in cooperation with the side walls to form an inclined ramp portion communicating with the interior of the container, with the margin of the one end and cooperating side walls terminating in a projecting transverse body engaging rim narrower than the transverse width of the container. The width of the projecting transverse body engaging rim has a preselected dimension for comfortably transversely contacting and engaging the female user's vaginal area. The height of the projecting transverse rim has a preselected dimension above the bottom or base of the urinal for engaging the user's vaginal area posterior of the urethra when the container is placed between the user's upper thighs and resting on the surface upon which the female is reclining. When the container's projecting transverse rim is firmly pressed into sealing contact with the user's vaginal area posterior to the urethra and retained in such position, the container collects urine discharged initially in a stream from the user's urethra and urine draining down onto the inclined ramp surface into the interior of the open container.

In accordance with a further principle of this invention, the projecting transverse rim has a smooth, rounded cross-section for comfortably and sealingly engaging the female vaginal area during use.

In accordance with a further principle of this invention, the bottom of the female urinal container has a transversely disposed ledge section adjacent the other transverse end wall. The transversely disposed ledge section projects upwardly into the container interior and forms an external transverse shoulder for permitting grasping of the other end of the container by hand for manipulating and transporting the container.

BRIEF DESCRIPTION OF THE DRAWINGS

In order that the manner in which the above-recited advantages and features of the invention are attained can be understood in detail, a more particular description of the invention may be had by reference to specific embodiments thereof which are illustrated in the accompanying drawings, which drawings form a part of this specification.

In the drawings:

FIG. 4 is a side illustrative view of the urinal in use by a female in a reclining position.

FIG. 5 is a frontal illustration of the urinal being used by a female in a reclining position.

DETAILED DESCRIPTION OF THE PREFERRED EMBODIMENTS

Figure 3:
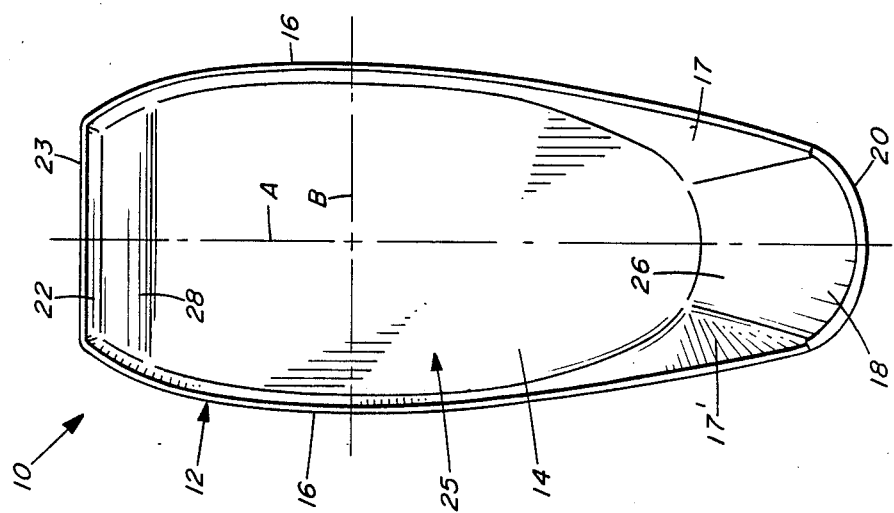
FIG. 3 is a top plan view of the female urinal according to this invention.
Figure 1:
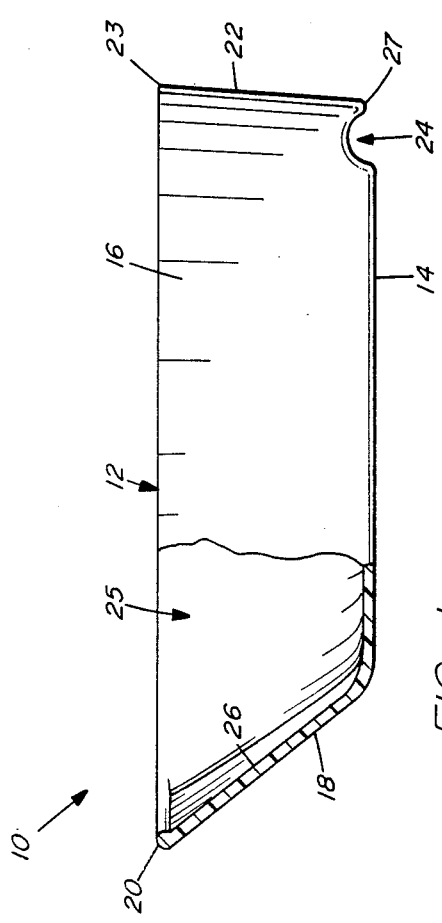
FIG. 1 is a side view, partially in vertical cross-section of the female urinal.
Figure 2:
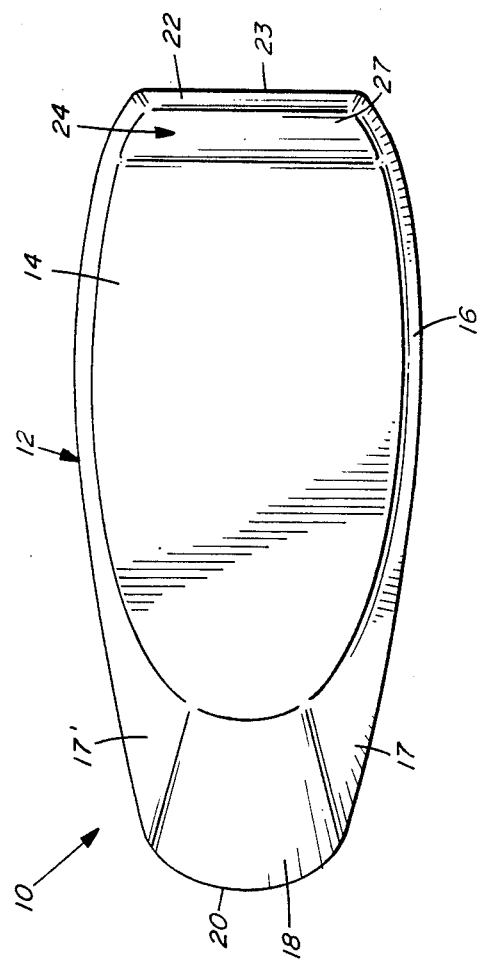
FIG. 2 is a bottom view of the female urinal according to this invention.

Referring now to FIGS. 1, 2 and 3, the structure of the female urinal 10 according to this invention will be described in detail. Urinal 10 comprises a generally rectangular or boat-shaped container 12 that has a longitudinal axis A substantially longer than its transverse axis B, with the width of the container 12 having a dimension preselected for comfortable placement between the upper thighs of a reclining female user (see FIGS. 4 and 5). The container 12 has a relatively flat bottom or base portion 14, continuous longitudinal side walls 16, and transverse end walls 18 and 22 integrally attached to the periphery of the bottom portion 14 and extending upwardly therefrom to form an open container having an interior volume 25.

One of the transversely disposed end walls 18 slants upwardly and outwardly from the bottom 14 in cooperation with the side walls 16 to form an inclined ramp 26 communicating with the interior 25 of the container 12. The ramp portion 26 (end wall 18) terminates in an outer margin 20 co-terminous with the outer margins of the wall portions 17 and 17' immediately adjacent the end wall 18. In other words, as illustrated in FIGS. 2 and 3, wall portions 17 and 17' are that portion of the side walls 16 which curve toward the interior of the container to meet the side of the ramp 18. The outer margin 20 of the end wall 18 forms a projecting generally transverse body engaging rim that is narrower than the transverse width of the container 12. The other end wall 22 and the side walls 16 project upwardly and slant slightly outwardly, which, when coupled with the "open" container 12 feature, permits the containers to be "stacked" or "nested" together to save packaging and storage space.

With respect to a female user, the container 12 must have a design that will prevent seepage of urine upon the user and the soiling of the user's clothing or bed clothes, and collect an initial discharged stream of urine from the urethra. Further, some means must be employed to prevent urine from seeping along the labia majora toward the anus and inflaming sensitive tissues which may also become infected. The flesh at and around the vagina and of the labia majora is of soft and conformable tissue. The projecting transverse rim 20 has a smooth, rounded cross-section and preferably an arcuately-shaped outer margin that when firmly pressed against the soft tissue of the vaginal area posterior to the user's urethra will create a good seal to the flow or seepage of urine. The width of the projecting transverse rim 20 has a dimension preselected for comfortably transversely contacting and engaging the female user's vaginal tissue as will hereinafter be described in greater detail.

In addition, the height of the projecting transverse body engaging rim 20 above the bottom 14 has a dimension preselected for permitting engagement with the user's vaginal tissue posterior of the urethra when the container 12 is placed between the reclining user's upper thighs. As will hereinafter be described in greater detail, when rim 20 is firmly pressed into contact with the user's vaginal tissue posterior of the urethra and maintained in that position, the rim 20 functions as a seal with the depressed vaginal tissue to prevent drainage and seepage of urine posterior to the placement of the rim 20. Further, proper placement of rim 20 positions the container 12 for collecting the initial stream of urine discharged from the urethra and then collects urine drainage along the vaginal opening and labia majora into the ramp collecting surface 26 and then into the interior 25 of the container 12. While rim 20 has been described as having a smooth, rounded cross-section, the cross-section configuration may take any convenient, smooth generally rounded shape, as long as the rim 20 is not "sharp" or has too much of an "edge" thus causing discomfort to the user's sensitive vaginal tissues during use. In addition, while the rim 20 has been described as having a generally arcuately-shaped outer margin or edge, rim 20 can have any convenient configuration that will accomplish the necessary sealing function.

In addition, the urinal 10 (container 12) has a transversely disposed raised section or ledge 28 projecting upwardly into the interior 25 of the container 12 for forming an external transverse shoulder 24 with a downwardly projecting rim 27. The upper edge 23 of the other end wall 22 cooperates with the transverse shoulder 24 and rim 27 to permit easy grasping by hand of the container by the end wall 22 to provide a means for transporting and manipulating the container 12.

The container 12 is preferably injection molded of a plastic polymer material which has sufficient stiffening polymers added to add strength and to make the container rigid yet somewhat flexible. If the container is constructed of plastic that is too soft and flexible, the container walls will flex too much and permit spillage when a container carrying a quantity of urine is attempted to be transported for testing or disposal. In the configuration shown in FIGS. 1, 2 and 3, a plurality of urinal containers 12 may be "nested" together for packaging and transport to save storage and packaging space. However, container 12 may be constructed of any suitable material as long as the aforementioned strength and rigidity requirements are met.

In a preferred embodiment, the elongated generally rectangular or boat-shaped urinal 10 has a longitudinal length between transverse edges 20 and 23 of ten (10) inches, and a transverse width between the spaced longitudinal side walls 16 of four (4) inches. The width of the projecting transverse rim 20 is about one and one-half (1.5) inches, while the height of the rim 20 is approximately two and one-half (2.5) inches above the level of the container bottom 14. An overall wall thickness of approximately 3/32 inches, and a 3/32-inch rounded smooth radius in cross-section of the rim 20 has been found to be convenient for strength, rigidity and comfort. However, containers 12 could be constructed in other similar configurations and in differing dimensions to accommodate different size female users.

Referring now to FIGS. 4 and 5, illustrated views of the use of the female urinal 10 are shown. With a female resting in a supine position on a horizontal surface 30, the female's thighs may be conveniently spread to receive and accommodate the elongated container 12. With the container 12 resting on the horizontal surface 30, the projecting transverse rim 20 is positioned in contact with the vaginal tissue 32 posterior of the female urethra 34 as shown in FIG. 4. If the edge 20 is firmly pressed into contact with the lower vaginal area tissue (see FIG. 4), the container 12 may be retained in place by the user grasping and holding the sides 16 of the container with her thighs, or the container 12 may be held in place by hand by a third party. By pressing the projecting transverse rim 20 firmly against the lower vaginal area tissue 32, posterior of the urethra 34, the rounded edge 20 sealingly engages the vaginal portion of the user's body and positions the ramp or throat surface 26 to collect urine as hereinabove described, and prevent leakage and drainage of the urine around the rim 20. After urination, the "handle" end 22 of the container may be grasped between the upper edge 23 and the lower bottom ledge or shoulder 24 and rim 27 for removing the container 12 from between the thighs of the user for transport of the urine for testing or disposal.

Numerous variations and modifications may be made in the structure herein described without departing from the present invention. Accordingly, it should be clearly understood that the forms of the invention herein described and shown in the figures of the accompanying drawings are illustrative only and are not intended to limit the scope of the invention.

I claim:

1. A urinal for use by a female when reclining in a prone position on a bed or other reclining surface, comprising
    a generally rectangular-shaped container having an open top and a longitudinal length dimension at least twice the dimension of the transverse width of said container, said transverse width of said container having a relatively narrow dimension selected for comfortable longitudinal placement between the upper thighs of a user when in the reclining position, said open top container comprising,
    a relatively flat bottom portion,
    continuous longitudinal side and transverse end walls integrally attached to said bottom portion and projecting upwardly therefrom which terminate in an edge to define said open top, and
    one of said transversely disposed end walls having at least a portion thereof slanting upwardly and outwardly from said bottom portion co-terminus with said side walls to form an inclined ramp portion communicating with the interior of said container, said side walls at said end wall curving toward the interior of said container to join the sides of said ramp, the outer margin of said inclined ramp portion terminating in a longitudinally projecting transverse rim section of said edge having a preselected transverse dimension narrower than the transverse width of said container and selected for comfortably engaging the soft tissue of the lower portion of the user's vaginal area for insuring sufficient transverse surface contact therewith for forming a seal therebetween, the height of said projecting transverse rim section above said bottom portion having a preselected dimension generally less than the transverse width of said container for engaging the user's vaginal area in a location posterior of the urethra when said container is placed between the user's upper thighs and resting on the reclining surface, wherein when said container projecting transverse rim section is firmly pressed into sealing contact with said vaginal area posterior of the urethra and retained in such position between the user's thighs, said container collects urine discharged initially in a stream from the urethra and urine that drains down unto said inclined ramp surface into the interior of said container.

2. The female urinal as described in claim 1, wherein said projecting transverse rim has a smooth rounded cross-section for comfortably and sealingly engaging the vaginal area during use.

3. The female urinal as described in claim 1, wherein said container bottom portion has a transversely raised ledge section adjacent the other transverse end wall projecting upwardly into said container interior and forming an external transverse shoulder for permitting hand grasping of said other end of said container for manipulating and transporting said container.

4. The female urinal as described in claim 1, wherein said side walls and other end slant slightly outwardly from the vertical for permitting a plurality of urinals to nest together.

5. A urinal for use by a female when reclining in a prone position on a bed or other reclining surface, comprising
    a generally rectangular-shaped container having an open top and a longitudinal dimension at least twice the transverse dimension of said container, said transverse dimension being relatively narrow and selected for comfortable longitudinal placement between the upper thighs of a user when a horizontal position, said open top container comprising,
    a relatively flat bottom portion,
    continuous longitudinal side and transverse end walls integrally attached to said bottom portion and extending upwardly therefrom which terminate in an edge to form said open top,
    one of said transversely disposed end walls having at least a portion thereof slanting upwardly and outwardly from said bottom portion co-terminus with said side walls to form an inclined ramp portion communicating with the interior of said container, said side walls at said end wall curving toward the interior of said container to join the sides of said ramp, the outer margin of said ramp portion terminating in a longitudinally projecting transverse rim having a preselected transverse dimension narrower than the transverse width of said container and selected for comfortably engaging the soft tissue of the lower portion of the user's vaginal area for insuring sufficient transverse surface contact therewith for forming a seal therebetween, the height of said projecting transverse rim above said bottom portion having a preselected dimension generally less than the transverse width of said container for engaging the user's vaginal area in a location below the urethra when said container is placed between the user's upper thighs and supported on the reclining surface,
    said projecting transverse rim having a smooth rounded cross-section, and
    said container bottom portion having a transversely raised ledge section adjacent said other end wall and projecting upwardly into said container interior for forming an external transverse shoulder for permitting hand grasping of said other end of said container for manipulating and transporting said container,
    wherein when said container projecting transverse rim is firmly pressed into sealing contact with said vaginal area below the urethra and retained in such position between the user's thighs, said container collects urine discharged from the reclining user's urethra.

6. The female urinal as described in claim 5, wherein said side walls and other end slant slightly outwardly from the vertical for permitting a plurality of urinals to nest together.

7. The female urinal as described in claim 5, wherein said preselected transverse dimension of said projecting rim section is generally less than one-half said transverse dimension of said container.

8. A urinal for use by a female when reclining in a prone position on a bed or other reclining surface, comprising a generally rectangular-shaped container having an open top and a longitudinal length dimension at least twice the dimension of the transverse width of said container, said transverse width of said container having a relatively narrow dimension selected for comfortable longitudinal placement between the upper thighs of a user when in the reclining position, said open top container comprising, a relatively flat bottom portion, continuous longitudinal side and transverse end walls integrally attached to said bottom portion and projecting upwardly therefrom which terminate in an edge to define said open top, and one of said transversely disposed end walls having at least a portion thereof slanting upwardly and outwardly from said bottom portion co-terminus with said side walls to form an inclined ramp portion communicating with the interior of said container, said side walls at said end wall curving toward the interior of said container to join the sides of said ramp, the outer margin of said inclined ramp portion terminating in a longitudinally projecting transverse rim section of said edge having a preselected transverse dimension narrower than the transverse width of said container and selected for comfortably engaging the soft tissue of the lower portion of the user's vaginal area for insuring sufficient transverse surface contact therewith for forming a seal therebetween, the height of said projecting transverse rim section being about two and one-half inches above said bottom portion, wherein when said container projecting transverse rim section is firmly pressed into sealing contact with said vaginal area posterior of the urethra and retained in such position between the user's thighs, said container collects urine that drains down unto said inclined ramp surface into the interior of said container.

9. The female urinal as described in claim 8, wherein said side walls and other end slant slightly outwardly from the vertical for permitting a plurality of urinals to nest together.

* * * * *